United States Patent [19]

Glamkowski et al.

[11] Patent Number: 5,563,272
[45] Date of Patent: Oct. 8, 1996

[54] 5,6-DIHYDRO-4H-IMIDAZO[4,5,1-IJ]QUINOLINES

[75] Inventors: Edward J. Glamkowski, Warren; Brian S. Freed, Phillipsburg, both of N.J.

[73] Assignee: Hoechst-Roussel Pharmaceuticals Inc., Somerville, N.J.

[21] Appl. No.: 455,465

[22] Filed: May 31, 1995

Related U.S. Application Data

[62] Division of Ser. No. 304,041, Sep. 9, 1994, Pat. No. 5,500,423.

[51] Int. Cl.⁶ .................................. C07D 401/12
[52] U.S. Cl. ..................... 546/171; 546/84; 544/60
[58] Field of Search ................................ 546/171

[56] References Cited

U.S. PATENT DOCUMENTS

| | | | |
|---|---|---|---|
| 3,142,679 | 7/1964 | Barrett et al. | 546/171 |
| 3,200,123 | 8/1965 | Richardson et al. | 546/84 |
| 3,975,531 | 8/1976 | Welstead, Jr. et al. | 514/416 |
| 4,209,519 | 6/1980 | Kinnamon | 546/171 |
| 5,064,852 | 11/1991 | Howard, Jr. et al. | 514/409 |

FOREIGN PATENT DOCUMENTS 54363  3/1988  Japan ..................... 546/171

OTHER PUBLICATIONS

L. M. Werbel, et al., Journal of Heterocyclic Chemistry, 5, 371 (1968) entitled "Synthesis of 5,6–Dihydro–8–methoxy–4H–imidazol[4,5–ij]quinolines and Some Related Ring Systems".

M. Protiva, et al., Collection Czechoslovak Chemical Communications, 50, 1888 (1985) entitled "Cyclic Amidines from Benzic, d[indole and 4,5–Dihydro–3H–1–Benzazepine including Some Related Compounds: Synthesis and Pharmacological Screening".

A. Richardson, Jr., Journal Org. Chem. 28(10) 2581–7 (1963) entitled "The Synthesis and Chemistry of Certain 2–substituted 5,6–dihydroimidazo, oxazolo–, and thiazolo[ij]quinolines".

Primary Examiner—Emily Bernhardt
Attorney, Agent, or Firm—Raymond R. Wittekind

[57] ABSTRACT

Novel 5,6-dihydro-4H-imidazo[4,5,1-ij]quinolines, intermediates and processes for the preparation thereof, and methods for alleviating pain utilizing compounds or compositions thereof are disclosed.

2 Claims, No Drawings

5,6-DIHYDRO-4H-IMIDAZO[4,5,1-IJ]QUINOLINES

This application is a divisional of U.S. patent application Ser. No. 08/304,041 filed Sep. 9, 1994, now U.S. Pat. No. 5,500,423 issued Mar. 19, 1996.

The present invention relates to novel 5,6-dihydro-4H-imidazo[4,5,1-ij]quinolines. More particularly, the present invention relates to 2-substituted-5,6-dihydro-4H-imidazo[4,5,1-ij]quinolines of formula 1

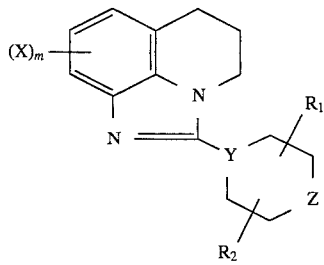

wherein:
(a) X is hydrogen, loweralkyl, loweralkoxy, halogen, or trifluoromethyl, and m is 1 or 2;
(b) $R_1$ is hydrogen or loweralkyl;
(c) $R_2$ is hydrogen, loweralkyl, or a group of the formula

wherein X and m are as above;
(d) Y is CH or N;
(e) Z is O, S, $CHR_3$, wherein $R_3$ is hydrogen, a group of the formula

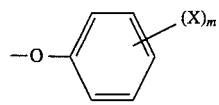

wherein X and m are as above, or a group of the formula $N(R_4)_2$ wherein $R_4$ is loweralkyl, or $NR_5$ wherein $R_5$ is hydrogen, loweralkyl, a group of the formula

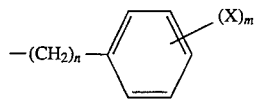

wherein X and m are as above and n is 0, 1, or 2, a group of the formula

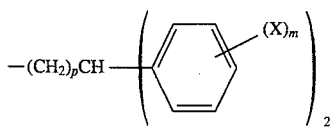

wherein X and m are as above and p is 0, 1, 2 or 3, a group of the formula $R_6CO-$ wherein $R_6$ is hydrogen or loweralkyl, or a group of the formula $R_7OCO-$ wherein $R_7$ is loweralkyl; a pharmaceutically acceptable salt thereof, or the geometric or the optical isomers thereof, which are useful as analgetic agents, alone or in combination with inert pain-alleviating adjuvants.

Subgeneric to the 2-substituted-5,6-dihydro-4H-imidazo[4,5,1-ij]quinolines of the present invention are those compounds wherein:
(a) Y is CH; and
(b) Y is N.

The present invention also relates to 4-[5,6-dihydro-4H-imidazo[4,5, 1-ij]quinolin-2-yl]piperidines of formula 5

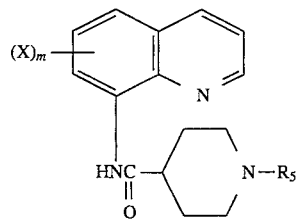

wherein $R_5$, X, and m are as hereinabovedescribed, useful as intermediates for the synthesis of the hereinbeforementioned 2-substituted-5,6-dihydro-4H-imidazo[4,5,1-ij]quinolines.

As used through the specification and appended claims, the term "alkyl" refers to a straight or branched chain hydrocarbon radical containing no unsaturation and having 1 to 10 carbon atoms such as methyl, ethyl, 1-propyl, 2-propyl, 1-butyl, 1-pentyl, 2-pentyl, 3-hexyl, 4-heptyl, 2-octyl, 3-nonyl, 4-decyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy, 2-methyloctoxy, octoxy, decoxy and the like; the term "halogen" refers to a member of the family fluorine, chlorine, bromine or iodine. The term "lower" as applied to any of the aforementioned groups refers to a group having a carbon skeleton containing up to and including 7 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diasteromeric salts of those instant compounds characterized by the presence of a basic amino group and an optically active acid, or by the synthesis from optically active precursors.

The present invention comprehends all optical isomers and racetalc forms thereof and all geometric isomers of the compounds disclosed and claimed herein. The formulas of the compounds shown herein are intended to encompass all possible geometric and optical isomers of the compounds so depicted.

The novel 2-substituted-5,6-dihydro-4H-imidazo[4,5,1-ij]quinoline 1 of the present invention is synthesized by the processes illustrated in the Reaction Scheme.

REACTION SCHEME

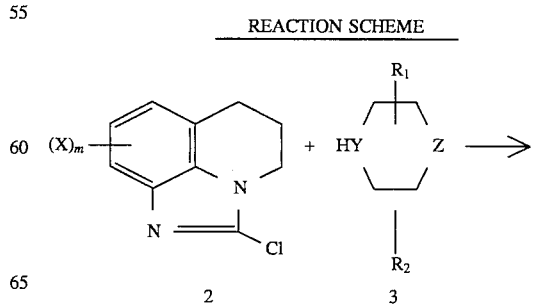

-continued
REACTION SCHEME

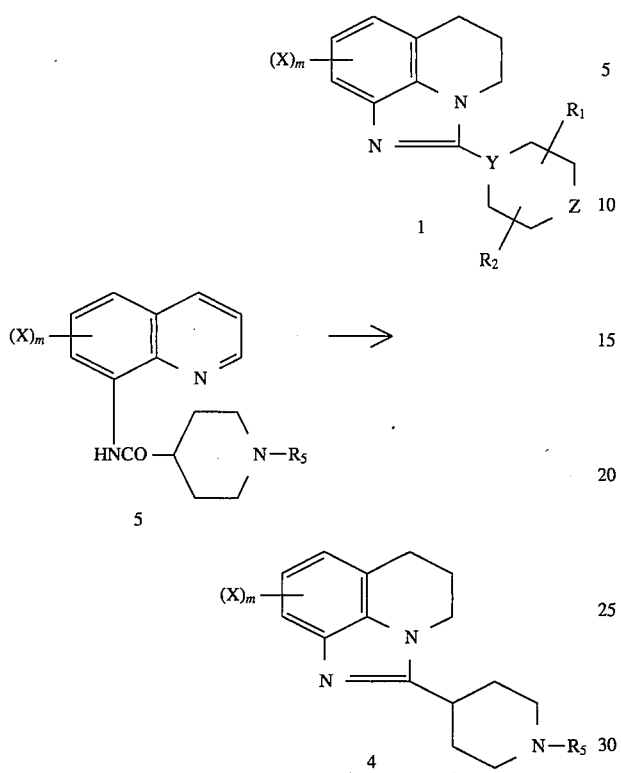

wherein $R_1$, $R_2$, $R_5$, X, Y, Z and m are as described herein.

To gain entry into the 2-substituted-5,6-dihydro-4H-imidazo[4,5,1-ij]quinoline series 1 wherein Y is N, a 2-chloro-5,6-dihydro-4H-imidazo[4,5,1-ij]quinoline 2, the preparation of which is described in L. M. Werbel, et al., Journal of Heterocyclic Chemistry, 5, 371 (1968), is condensed with a cyclic amine 3, wherein Y is N to provide the ultimate 2-substituted imidazo quinoline 1. The condensation is conveniently carded out by heating a mixture of the 2-chloroimidazoquinoline 2 with the cyclic amine 3 at an elevated temperature with or without an acid scavenger or an added solvent. When the reaction is carried out without an added solvent, excess cyclic amine (about 2 to about 20 moles of cyclic amine 3 to 2-chloroimidazole 2) is generally employed. When the reaction is carried out with an added solvent, about equimolar amounts of cyclic amine 3 and 2-chloroimidazole 2 and an acid scavenger are employed. Among added solvents, there may be mentioned aprotic dipolar solvents such as dimethylacetamide, dimethylformamide, and hexamethylphosphoramide, dimethylformamide being preferred. Among acid scavengers, there may be mentioned aliphatic tertiary amines such as triethylamine, di-2-propylethylamine, tri-2-propylamine, aromatic tertiary amines such as pyridine, and methylpyridines such as picoline, lutidine, collidine, and the like. Aliphatic tertiary amines are preferred; triethylamine and di-2-propylethylamine are most preferred. Elevated reaction temperatures, while not narrowly critical, promote the condensation and generally include the reflux temperature of the reaction medium, or fall within the range of about 100° to about 150° C.

In the alternative, the ultimate 5,6-dihydro-4H-imidazo[4,5,1-ij]quinolines 1 wherein Y is CH are prepared, for example, by reductive cyclization of a quinolin-8-yl-carboxamide 5, the preparation of which is also described in L. M. Werbel, et al., ibid., 5, 371 (1968), to an imidazo-5,6-dihydroquinoline 4. The reductive cyclization is accomplished by contacting a carboxamide 5 with hydrogen in the presence of a catalyst such as platinum, platinum oxide, palladium, mthenium, rhodium, or strontium, free or supported, for example, on carbon or calcium carbonate in an organic solvent, such as glacial acetic acid, typically at room temperature. Platinum oxide is the preferred catalyst.

Modification of the substituents of the ultimate product 1 (including 4) may be effected by conventional processes. For example, hydrolysis of 2-substituted imidazoles 1 and 4 wherein $R_4$ is $R_6CO$ wherein $R_6$ is hydrogen or loweralkyl is perfected by treating the carboxamide 1 or 4 with a hydrohalic acid such as hydrobromic acid at the reflux temperature of the reaction medium, and alkylation of an ultimate product 1 or 4 wherein $R_4$ is hydrogen is accomplished by reductive alkylation with formaldehyde-formic acid to provide the N-methyl derivatives 1 and 4 wherein $R_4$ is methyl.

The 5,6-dihydro-4H-imidazo[4,5,1-ij]quinolines of the present invention are useful as analgetics due to their ability to alleviate pain in mammals. The analgetic utility is demonstrated in the phenyl-p-quinone writhing assay in mice, a standard assay for analgesia [Proceedings of the Society for Experimental Biology and Medicine, 95, 729 (1957)]. Thus, for instance, at a subcutaneous dose of 20 mg/kg, administered 30 minutes before injection of phenylquinone, the present compounds elicit the percent inhibition of writhing in mice shown below:

| Compound | % Inhibition of Writhing |
| --- | --- |
| 5,6-dihydro-2-(1-piperidinyl)-4H-imidazo-[4,5,1-ij]quinoline | 68 |
| 4-[4,4-bis(4-fluorophenyl)-butyl]-1-piperazinyl-5,6-dihydro-4H-imidazo-[4,5,1-ij]quinoline | 43 |
| 1-acetyl-4-[5,6-dihydro-4H-imidazo-[4,5,1-ij]quinolin-2-yl]-piperidine | 51 |
| 5,6-dihydro-2-(l-piperazinyl)-4H-imidazo[4,5,1-ij]quinoline | 57 |
| 5,6-dihydro-2-[4-phenylethyl-1-piperazinyl]-4H-imidazo[4,5,1-ij]-quinoline | 45 |
| 5,6-dihydro-2-(4-thiomorpholinyl)-4H-imidazo[4,5,1-ij]quinoline | 53 |
| ethyl-4-[5,6-dihydro-4H-imidazo-[4,5,1-ij]quinolin-2-yl]-1-piperazine-carboxylate | 47 |
| 2-(4-piperdinyl)-5,6-dihydro-4H-imidazo-[4,5,1-ij]quinoline | 31 |
| 5,6-dihydro-2-[4-dimethylamino-1-piperidinyl]-4H-imidazo[4,5,1-ij]quinoline | 48 |
| propoxyphene (standard) | 19% @ 5.0 mg/kg s.c. |

Analgesia production is achieved when the present 5,6-dihydro-4H-imidazo[4,5,1-ij]quinolines are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Effective amounts of the present invention may be administered to a subject by any one of various methods, for example, orally as in capsules or tablets, parenterally in the form of sterile solutions or suspensions, and in some cases intravenously in the form of sterile solutions. The 5,6-dihydro-4H-imidazo[4,5,1-ij]quinolines of the present invention, while effective themselves, may be formulated and administered in the form of their pharmaceutically acceptable addition salts for the purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of the invention may be administered orally, for example, with an inert diluent or with an edible carrier. They may be enclosed in gelatin capsules or compressed in tablets. For the purpose of oral therapeutic administration, the aforesaid compounds may be incorporated with excipient and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants such as ascorbic acid or sodium bisulfite; chelating agents such an ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Included among compounds of the invention are:

(a) 5,6-dihydro-8-ethyl-2-[4-methyl-1-piperazinyl]-4H-imidazo[4,5, 1-ij]quinoline;

(b) 5,6-dihydro-8-ethoxy-2-[4-methyl-1-piperazinyl]-4H-imidazo-[4,5,1-ij]quinoline;

(c) 5,6-dihydro-8-fluoro-2-[4-methyl-1-piperazinyl]-4H-imidazo-[4,5,1-ij]quinoline;

(d) 5,6-dihydro-2-[4-methyl-1-piperazinyl]-4H-imidazo [4,5,1-ij]-8 -trifluoromethylquinoline;

(e) 5,6-dihydro-8,9-dimethyl-2-[4-methyl-1-piperazinyl]-4H-imidazo-[4,5,1-ij]quinoline;

(f) 1-acetyl-4-[5,6-dihydro-4H-imidazo[4,5,1-ij]-6-methylquinolin-2-yl]piperidine;

(g) 1-acetyl-4-[5,6-dihydro-4H-imidazo[4,5,1-ij]-6-methoxyquinolin-2-yl]piperidine;

(h) 1-acetyl-4-[5,6-dihydro-4H-imidazo[4,5,1-ij]-6-chloroquinolin-2-yl]piperidine and (i) 1 -acetyl-4-[5,6-dihydro-4H-imidazo 4,5,1 -ij]-6-trifluoromethylquinolin-2-yl]piperidine.

The following examples are for illustrative purposes only and are not to be construed as limiting the invention. All temperatures are given in degrees centigrade (°C).

EXAMPLE 1

8-Amino-1,2,3,4-Tetrahydroquinoline

To a solution of 20.00 g of 8-aminoquinoline in boiling absolute ethanol (400 ml) was added 44.74 g of sodium pellets over 20 mins, with stirring, until the sodium is dissolved. The reaction mixture was poured into water (50 ml) and concentrated. The residue was diluted with sodium bicarbonate solution and the mixture was extracted with dichloromethane. The extracts were dried over anhydrous magnesium sulfate, filtered, and the filtrate was evaporated. The residue was distilled under vacuum to give 10.77 g (52.3%) of product.

EXAMPLE 2

5,6-Dihydro-4H-imidazo[4,5,1-ij]quinolin-2(1H)-one

To a solution of 10.77 g of 8-amino- 1,2,3,4-tetrahydroquinoline in glacial acetic acid (30 ml) was added dropwise a 21.75% solution of phosgene in chlorobenzene (30 ml), under nitrogen, with stirring. After the addition was complete, the mixture was heated under reflux, with stirring for one hr and evaporated. The residue was taken up in 10% ammonium hydroxide solution (75 ml) and extracted with dichloromethane. The organic extracts were dried over anhydrous magnesium sulfate, filtered, and the filtrate was evaporated. Ether was added to the residue and the mixture was chilled. The precipitate was collected to give 11.2 g (88%) of product.

EXAMPLE 3

2-Chloro-5,6-dihydro-4H-imidazo[4,5,1-ij]quinoline

A slurry of 13.60 g of 5,6-dihydro-4H-imidazo[4,5,1-ij]quinolin-2(1H)-one and phosphorus oxychloride (35 ml) was heated under reflux, with stirring, for 1.5 hrs and stirred at ambient temperature overnight. 10% Ammonium hydroxide (100 ml) and ice were added. The mixture was filtered, and the filtrate was extracted with dichloromethane. The organic extracts were washed with brine, dried over anhydrous magnesium sulfate and filtered. The filtrate was evaporated. The residue was purified by flash chromatography (silica; 10:1 dichloromethane-ethyl acetate). The appropriate fractions were collected and evaporated to give 9.90 g (65.8%) of product, mp 78° C.

EXAMPLE 4

5,6-Dihydro-2-(4-methyl-1-piperazinyl)-4H-imidazo[4,5,1-ij]quinoline

A solution of 2-chloro-5,6-dihydro-4H-imidazo[4,5,1-ij] quinoline (4.30 g) in 20 ml of N-methylpiperazine (18.06 g) was heated under reflux, under nitrogen, with stirring. After 30 mins, the solution was diluted with sodium bicarbonate solution (100 ml) and water (200 ml). The aqueous solution was extracted with chloroform. The organic phase was dried over anhydrous magnesium sulfate and concentrated. The residue was purified by high performance liquid chromatography (silica gel; methanol). The appropriate fractions were collected and evaporated. The residue was crystallized from ether-petroleum ether to give 4.0 g (70%) of product, mp 112°–113° C.

Analysis:

| | | | |
|---|---|---|---|
| Calculated for $C_{15}H_{20}N_4$: | 70.28% C | 7.86% H | 21.86% N |
| Found: | 70.06% C | 7.81% H | 21.87% N |

EXAMPLE 5

5,6-Dihydro-2-(4-morpholinyl)-4H-imidazo[4,5,1-ij]quinoline

A solution of 2-chloro-5,6-dihydro-4H-imidazo [4,5,1-ij] quinoline (2.50 g) in morpholine (15 ml) was heated under reflux, under nitrogen, with stirring. After one hr, the solution was diluted with sodium bicarbonate solution (100 ml) and water (100 ml). The aqueous solution was extracted with chloroform. The organic phase was dried over anhydrous magnesium sulfate and concentrated. The residue was purified by high performance liquid chromatography (silica gel; ethyl acetate). The appropriate fractions were collected and concentrated. The residue was crystallized from ether to give 2.1 g (67%) of product, mp 93°–94° C.

Analysis:

| | | | |
|---|---|---|---|
| Calculated for $C_{14}H_{17}N_3O$: | 69.11% C | 7.04% H | 17.27% N |
| Found: | 69.17% C | 6.93% H | 17.51% H |

EXAMPLE 6

5,6-Dihydro-2-(1-piperidinyl)-4H-imidazo[4,5.1-ij]quinoline hydrochloride

A solution of 2-chloro-5,6-dihydro-4H-imidazo[4,5,1-ij] quinoline (3.5 g) in piperidine (20 ml) was stirred under reflux, under nitrogen, for four hrs. The reaction mixture was quenched with dilute sodium bicarbonate solution (200 ml) and the aqueous suspension was extracted with chloroform. The combined organic extracts were dried over anhydrous magnesium sulfate and concentrated. The residue was purified by high performance liquid chromatography (silica gel; 3:1 dichloromethane-ethyl acetate). The appropriate fractions were collected and concentrated. This residue was dissolved in ether and treated dropwise with a solution of hydrogen chloride/ether. The precipitate was collected and washed with ether to give 4.3 g (85%) of product, mp 260° C.

Analysis:

| | | | |
|---|---|---|---|
| Calculated for $C_{15}H_{19}N_3.HCl$: | 64.85% C | 7.26% H | 15.13% N |
| Found: | 65.00% C | 7.54% H | 15.41% N |

EXAMPLE 7

7-Bromo-5,6-dihydro-2-(4-methyl-1-piperazinyi)-4H-imidazo[4,5,1-ij]quinoline

A solution of 7-bromo-2-chloro-5,6-dihydro-4H-imidazo [4,5,1-ij]quinoline (3.00 g) in N-methylpiperazine (20 ml) was stirred under reflux, under nitrogen, for two hrs. The reaction mixture was quenched with dilute sodium bicarbonate solution (200 ml) and extracted with chloroform. The combined organic extracts were dried over anhydrous magnesium sulfate, filtered, and the filtrate was concentrated. The residue was purified by high performance liquid chromatography (silica gel; 7:1 dichloromethane-methanol). The appropriate fractions were collected and evaporated. The residue was recrystallized from ethyl acetate-ether to give 2.1 g (57%) of product, mp 132°–133° C.

Analysis:

| | | | |
|---|---|---|---|
| Calculated for $C_{15}H_{19}BrN_4$: | 53.74% C | 5.71% H | 16.71% N |
| Found: | 53.71% C | 5.72% H | 16.93% N |

EXAMPLE 8

5,6-Dihydro-8-methyl-2-(4-methyl-1-piperazinyl)-4H-imidazo[4,5,1-ij]quinoline

A solution of 2-chloro-5,6-dihydro-8-methyl-4H-imidazo [4,5,1-ij]quinoline (3.50 g) in N-methylpiperazine (20 ml) was stirred, under nitrogen, under reflux for 1.5 hrs. The reaction mixture was quenched with saturated sodium bicarbonate solution (200 ml) and extracted with chloroform. The combined organic extracts were dried over anhydrous magnesium sulfate, filtered, and the filtrate was concentrated. The residue was purified by high performance liquid chromatography (silica; 9:1 dichloromethane-methanol). The appropriate fractions were collected and evaporated. The residue was recrystallized from ethyl acetate to give 3.48 g (76%) of product, mp 164°–165° C.

Analysis:

| | | | |
|---|---|---|---|
| Calculated for $C_{16}H_{22}N_4$: | 71.07% C | 8.20% H | 20.72% N |
| Found: | 71.14% C | 8.11% H | 20.79% N |

EXAMPLE 9

5,6-Dihydro-2-(4-phenyl-1-piperazinyl)-4H-imidazo[4,5,1-ij]quinoline

A solution of 2-chloro-5,6-dihydro-4H-imidazo[4,5,1-ij]quinoline (3.00 g) in 1-phenylpiperazine (10 ml) was stirred at 100° C., under nitrogen, for five hrs. The reaction mixture was quenched with saturated sodium bicarbonate solution (200 ml) and extracted with chloroform. The combined organic extracts were dried over anhydrous magnesium sulfate, filtered, and the filtrate was concentrated. The residue was purified by high performance liquid chromatography (silica gel; 4:1 dichloromethane-ethyl acetate). The appropriate fractions were collected and evaporated. The residue was recrystallized from ethyl acetate to give 2.2 g (45%) of product, mp 168°–169° C.

Analysis:

| | | | |
|---|---|---|---|
| Calculated for $C_{20}H_{22}N_4$: | 75.44% C | 6.97% H | 17.60% N |
| Found: | 75.70% C | 6.90% H | 17.88% N |

EXAMPLE 10

4-[4,4-Bis(4-fluorophenyl)-butyl]-1-piperazinyl-5,6-dihydro-4H-imidazo[4,5,1-ij]quinoline A solution of 2-chloro-5,6-dihydro-4H-imidazo[4,5,1-ij]quinoline (3.00 g) and 1-[4,4-bis(4-fluorophenyl)-butyl]piperazine (4.60 g) was stirred at 135° C., under nitrogen, for 1.5 hrs. The reaction mixture was quenched with dilute sodium bicarbonate solution (300 ml) and extracted with dichloromethane. The combined organic extracts were dried over anhydrous magnesium sulfate, filtered, and the filtrate was concentrated. The residue was purified by high performance liquid chromatography (silica gel; 20:1 dichloromethane-methanol). The appropriate fractions were collected and evaporated. The residue was triturated with ether. The solid was collected and recrystallized from ethyl acetate to give 4.7 g (69%) of product, mp 138°–140° C.

Analysis:

| | | | |
|---|---|---|---|
| Calculated for $C_{30}H_{32}F_2N_4$: | 74.05% C | 6.63% H | 11.51% N |
| Found: | 73.95% C | 6.37% H | 11.78% N |

EXAMPLE 11

4-[5,6-Dihydro-4H-imidazo[4,5,1-ij]quinolin-2-yl]-1-piperazinecarboxaldehyde A solution of 2-chloro-5,6-dihydro-4H-imidazo[4,5,1-ij]quinoline (20.00 g) in 1-piperazinecarboxaldehyde (25.00 g) was stirred at 120° C., under nitrogen, for 1.5 hrs. The reaction mixture was quenched with dilute sodium bicarbonate solution (300 ml) and extracted with chloroform. The organic extracts were combined, washed with brine, dried over anhydrous magnesium sulfate and filtered. The filtrate was concentrated. The residue was purified by flash chromatography (silica gel; 25:1 dichloromethane-methanol). The appropriate fractions were collected and evaporated. The residue was recrystallized twice from ethyl acetate to give 18.1 g (64%) of product, mp 138°–139° C.

Analysis:

| | | | |
|---|---|---|---|
| Calculated for $C_{15}H_{18}N_4O$: | 66.64% C | 6.71% H | 20.73% N |
| Found: | 66.85% C | 6.77% H | 20.90% N |

EXAMPLE 12

5,6-Dihydro-2-(4-benzyl-1-piperazinyl)-4H-imidazo[4,5,1-ij]quinoline

A solution of 2-chloro-5,6-dihydro-4H-imidazo[4,5,1-ij]quinoline (3.00 g) in 1-benzylpiperazine (10 ml) was stirred at 100° C., under nitrogen, for four hrs. The reaction mixture was quenched with dilute sodium bicarbonate solution (300 ml) and extracted with dichloromethane. The combined organic extracts were dried over anhydrous magnesium sulfate, filtered, and the filtrate was concentrated. The residue was purified by high performance liquid chromatography (silica gel; 25:1 dichloromethane-methanol). The appropriate fractions were collected and evaporated. The residue was recrystallized from ethyl acetate to give 3.6 g (70%) of product, mp 157°–158° C.

Analysis:

| | | | |
|---|---|---|---|
| Calculated for $C_{21}H_{24}N_4$: | 75.87% C | 7.28% H | 16.85% N |
| Found: | 75.84% C | 7.11% H | 16.78% N |

EXAMPLE 13

2-[4-[3-(Trifluoromethyl)phenyl]-1-piperazinyl]-5,6-dihydro-4H-imidazo[4,5,1-ij]quinoline A solution of 2-chloro-5,6-dihydro-4H-imidazo[4,5,1-ij]quinoline (3.00 g) in 1-[3-(trifluoromethyl)phenyl]piperazine (5 ml) was stirred at 110° C., under nitrogen. After four hrs, chloroform (50 ml) was added, and the solution was stirred under reflux overnight. The reaction mixture was quenched with dilute sodium bicarbonate solution (200 ml) and extracted with chloroform. The combined organic extracts were dried over anhydrous magnesium sulfate, filtered, and the filtrate was evaporated. The residue was purified by high performance liquid chromatography (silica gel; 8:1 dichloromethane-ethyl acetate). The appropriate fractions were collected and evaporated. The residue was recrystallized from ethyl acetate to give 3.0 g (50%) of product, mp 158°–159° C.

Analysis:

| | | | |
|---|---|---|---|
| Calculated for: $C_{21}H_{21}F_3N_4$: | 65.27% C | 5.48% H | 14.50% N |
| Found: | 65.19% C | 5.43% H | 14.45% N |

EXAMPLE 14

5,6-Dihydro-2-(4-phenylethyl)-1-piperazinyl)-4H-imidazo[4,5,1-ij]quinoline

A solution of 2-chloro-5,6-dihydro-4H-imidazo[4,5,1-ij]quinoline (3.00 g) in 1-phenylethylpiperazine (8.00 g) was stirred at 110° C., under nitrogen, for two hrs. The reaction mixture was quenched with dilute sodium bicarbonate solution (300 ml) and extracted with dichloromethane. The combined organic extracts were dried over anhydrous magnesium sulfate, filtered, and the filtrate was evaporated. The residue was purified twice by flash chromatography first by silica gel using 25:1 dichloromethane-methanol, then by silica gel using 5:1 ethyl acetate-hexane followed by 100% ethyl acetate. In each case, the appropriate fractions were collected and evaporated. The residue was recrystallized from ethyl acetate-ether to give 3.85 g (71%) of product, mp 112°–113° C.

Analysis:

| | | | |
|---|---|---|---|
| Calculated for $C_{22}H_{26}N_4$: | 76.26% C | 7.57% H | 16.17% N |
| Found: | 76.27% C | 7.52% H | 16.09% N |

EXAMPLE 15

2-[4-(4-Bromophenoxy)-3-phenyl]-1-piperidinyl]-5,6-dihydro-4H-imidazo[4,5,1-ij]quinoline A solution of 2-chloro-5,6-dihydro-4H-imidazo[4,5,1-ij]quinoline (3.00 g), 4-(4-bromophenoxy)-3-phenylpiperidine (5.20 g), triethylamine (1.62 g) and dimethylformamide (50 ml) was stirred at 115° C., under nitrogen, overnight. The solution was poured onto ice water (600 ml) and the precipitate was collected. The precipitate was dissolved in dichloromethane and the solution was washed with brine, dried over anhydrous magnesium sulfate, filtered, and the filtrate was evaporated. The residue was triturated with ethyl acetate and then recrystallized from chloroform-ether to give 4.25 g (56%) of product, mp 188°–189° C.

Analysis:

| | | | |
|---|---|---|---|
| Calculated for $C_{27}H_{26}BrN_3O$: | 66.39% C | 5.37% H | 8.60% N |
| Found: | 65.75% C | 5.38% H | 8.52% N |

EXAMPLE 16

5,6-Dihydro-2-(4-thiomorpholinyl)-4H-imidazo[4,5,1-ij]quinoline hydrochloride

A solution of 2-chloro-5,6-dihydro-4H-imidazo[4,5,1-ij]quinoline (3.50 g) in thiomorpholine (10.0 g) was stirred at 120° C., under nitrogen, for two hrs. The reaction mixture was quenched with dilute sodium bicarbonate solution (300 ml) and extracted with dichloromethane. The combined organic extracts were dried over anhydrous magnesium sulfate, filtered, and the filtrate was evaporated. The residue was purified by flash chromatography (silica gel; 12:1 dichloromethane-ethyl acetate). The appropriate fractions were collected and evaporated. The residue was recrystallized from ethyl acetate-ether to give 4.2 g ((89%) of product as free base. The free base was dissolved in anhydrous ether and treated dropwise with ethereal hydrogen chloride solution. The precipitate was collected and recrystallized from methanol-ether to give 4.5 g (84%) of product, mp 235°–237° C.

Analysis:

| | | | |
|---|---|---|---|
| Calculated for $C_{14}H_{17}N_3S.HCl$: | 56.84% C | 6.13% H | 14.20% N |
| Found: | 56.89% C | 6.21% H | 14.25% N |

EXAMPLE 17

2-[4-[(4-Chlorophenyl)(phenyl)methyl]-1-piperazinyl]-5,6-dihydro-4H-imidazo[4,5,1-ij]quinoline hemifumarate A solution of 2-chloro-5,6-dihydro-4H-imidazo[4,5,1-ij]quinoline (3.00 g), 1-(4-chlorobenzhydryl)piperazine (4.59 g), diisopropylethylamine (2.07 g), and dimethylformamide (35 ml) was stirred at 100° C., under nitrogen, overnight. The solution was poured over ice water (400 ml) and the precipitate was collected. The precipitate was dissolved in chloroform (200 ml), and the solution was washed with brine. The organic phase was dried over anhydrous magnesium sulfate, filtered, and the filtrate was evaporated. The residue was triturated with hot ethyl acetate, chilled and filtered. The filter cake was dissolved in warm methanol, treated with a solution of fumaric acid in methanol, and concentrated. The collected solid was recrystallized from methanol-ether twice to give 3.2 g (41%) of product, mp 167°–169° C.

Analysis:

| | | | |
|---|---|---|---|
| Calculated for $C_{27}H_{27}ClN_4.0.5\ C_4H_4O_4$: | 69.52% C | 5.83% H | 11.18% N |
| Found: | 69.26% C | 5.76% H | 11.10% N |

EXAMPLE 18

Ethyl-4-[5,6-dihydro-4H-imidazo[4,5,1-ij]quinolin-2-yl]-1-piperazinecarboxylate fumarate A solution of 2-chloro-5,6-dihydro-4H-imidazo[4,5,1-ij]quinoline (5.00 g), ethyl-1-piperazinecarboxylate (4.11 g), diisopropylethylamine (3.36 g) and dimethylformamide (25 ml) was stirred at 110° C., under nitrogen, overnight. The reaction mixture was quenched with water (300 ml) and extracted with dichloromethane. The combined organic extracts were dried over anhydrous magnesium sulfate, filtered, and the filtrate was evaporated. The residue was purified by flash chromatography (silica gel; 2% methanol-dichloromethane). The appropriate fractions were collected and evaporated. The residue was treated with fumaric acid in warm methanol. The mixture was concentrated and the precipitate was recrystallized from methanol-ether to give 6.9 g (85%) of product, mp 174°–176° C.

Analysis:

| | | | |
|---|---|---|---|
| Calculated for $C_{17}H_{22}N_4O_2.C_4H_4O_4$: | 58.59% C | 6.09% H | 13.02% N |
| Found: | 58.64% C | 6.10% H | 13.03% N |

EXAMPLE 19

2-(1-Methyl-4-piperidinyl)-5,6-dihydro-4H-imidazo[4,5,1-ij]quinoline fumarate

A mixture of 2-(4-piperidinyl)-5,6-dihydro-4H-imidazo[4,5,1-ij]-quinoline (3.00 g) and formic acid (1.43 g) was stirred at 60° C., under nitrogen, as a solution of formaldehyde in water (1.12 g) was added in small portions. The reaction mixture was stirred for one hr at 60° C. and quenched with sodium bicarbonate solution (200 ml). The mixture was extracted with dichloromethane. The organic layers were combined, dried over anhydrous magnesium sulfate and evaporated. The residue was purified by flash chromatography (silica gel; 1% triethylamine-methanol). The appropriate fractions were collected and evaporated to give 2.90 g (91%) of product as the free base. The free base was combined with previously prepared material and fumaric acid in warm methanol was added. The mixture was concentrated and ether was added. The precipitate was recrystallized from methanol-ether to give 9.2 g of product, mp 225°–226° C.

Analysis:

| | | | |
|---|---|---|---|
| Calculated for $C_{16}H_{21}N_3.C_4H_4O_4$: | 64.67% C | 6.78% H | 11.31% N |
| Found: | 64.76% C | 6.87% H | 11.20% N |

EXAMPLE 20

5,6-Dihydro-2-(3,5-dimethyl-1-piperazinyl)-
4H-imidazo[4,5,1-ij]quinoline hemifumarate A solution of 2-chloro-5,6-dihydro-4H-imidazo[4,5,1-ij]quinoline (3.50 g), 2,6-dimethylpiperazine (2.17 g), diisopropylethylamine (2.46 g) and dimethylformamide (20 ml) was stirred at 100° C., under nitrogen, overnight. The reaction mixture was quenched with water (400 ml) and extracted with chloroform. The combined organic layers were dried over anhydrous magnesium sulfate, filtered and evaporated. The residue was purified by flash chromatography (silica gel; 10:1 dichloromethane-methanol). The appropriate fractions were collected and evaporated to give 2.84 g (58%) of product as the free base. The product free base was dissolved in warm methanol, treated with a solution of fumaric acid in methanol and the solution was concentrated. Ether was added. The crystals were collected and recrystallized from methanol-ether to give 2.7 g (45%) of product, mp 262°–264° C.

Analysis:

| | | | |
|---|---|---|---|
| Calculated for $C_{16}H_{22}N_4.0.5\ C_4H_4O_4$: | 65.83% C | 7.37% H | 17.06% N |
| Found: | 65.66% C | 7.35% H | 17.04% N |

EXAMPLE 21

2-[4-(2-Methoxyphenyl)-1-piperazinyl]-5,6-dihydro-
4H-imidazo[4,5,1-ij]quinoline hemifumarate A solution of 2-chloro-5,6-dihydro-4H-imidazo[4,5,1-ij]quinoline (3.00 g), 1-(2-methoxyphenyl)piperazine (3.08 g), diisopropylethylamine (2.07 g) and dimethylformamide (20 ml) was stirred at 105° C., under nitrogen, overnight. The reaction i mixture was quenched with ice-water (400 ml) and the precipitate collected. The precipitate was dissolved in dichloromethane and the solution washed with brine. The organic phase was dried over anhydrous magnesium sulfate, filtered, and the filtrate was evaporated. The residue was purified by flash chromatography (silica gel; 40:1 dichloromethane-methanol). The appropriate fractions were collected and evaporated. The residue was crystallized from ether. The crystals were dissolved in warm methanol, treated with a solution of fumaric acid in methanol and concentrated. Crystallization was induced with ether and the precipitate was recrystallized from methanol-ether to give 2.8 g (44%) of product, mp 199°–201° C.

Analysis:

| | | | |
|---|---|---|---|
| Calculated for $C_{21}H_{24}N_4O.0.5\ C_4H_4O_4$: | 67.96% C | 6.45% H | 13.78% N |
| Found: | 67.97% C | 6.59% H | 13.80% N |

EXAMPLE 22

5,6-Dihydro-2-(4-dimethylamino-1-piperidinyl)-
4H-imidazo[4,5,1-ij]quinoline fumarate A solution of 2-chloro-5,6-dihydro-4H-imidazo[4,5,1-ij]quinoline (3.00 g) in 4-dimethylaminopiperidine (6.00 g) was stirred at 100° C., under nitrogen, for two hrs. The reaction mixture was quenched with sodium bicarbonate solution (200 ml) and extracted with chloroform. The combined organic extracts were dried over anhydrous sodium sulfate, filtered, and the filtrate was evaporated. The residue was purified by flash chromatography (silica gel; 1% triethylamine-methanol) to give 2.7 g (61%) of product as the free base. The free base was dissolved in methanol, treated with a solution of fumaric acid in methanol and concentrated. Crystallization was induced with ether. The precipitate was recrystallized from methanol-ether to give 2.1 g (44%) of product, mp 197°–199° C.

Analysis:

| | | | |
|---|---|---|---|
| Calculated for $C_{17}H_{24}N_4.C_4H_4O_4$: | 62.98% C | 7.05% H | 13.99% N |
| Found: | 62.61% C | 6.97% H | 13.82% N |

EXAMPLE 23

1-Acetyl-N-(quinolin-8-yl)-4-piperidinecarboxamide

A solution of 8-aminoquinoline (48.50 g) in dimethylformamide (300 ml) was stirred at 80° C., under nitrogen, as a mixture of 1-acetylpiperidine-4-carbonyl chloride hydrochloride (106.30 g) and potassium carbonate (93.0 g) was added in portions. The slurry was stirred at 80° C. overnight, quenched with water (1200 ml) and extracted with dichloromethane. The extracts were dried over anhydrous magnesium sulfate, filtered, and the filtrate was evaporated. The residue was purified first by high performance liquid chromatography (silica; 25:1 dichloromethane-methanol), followed by flash chromatography (silica; 50:1 dichloromethane-methanol). The appropriate fractions were collected and evaporated to give 58.5 g (58.6%) of product, as an oil.

EXAMPLE 24

1-Acetyl-4-[5,6-dihydro-
4H-imidazo[4,5,1-ij]quinolin-2-yl]piperidine

A mixture of 1-acetyl-N-(quinolin-8-yl)-4-piperidinecarboxamide (51.28 g), glacial acetic acid (800 ml), and platinum oxide (4.00 g) was shaken under hydrogen at ambient temperature until the calculated amount of hydrogen was consumed. The platinum oxide was filtered through a bed of celite and the filter cake was washed with acetic acid. The filtrate was evaporated to ~200 ml, and was then stirred under reflux for four hrs, basified with 10% ammonium hydroxide solution and extracted with dichloromethane. The combined organic extracts were dried over anhydrous magnesium sulfate, filtered, and the filtrate was concentrated. The residue was combined with material from another reaction mixture. The combined residue was purified by high performance liquid chromatography (silica gel; 20:1 dichloromethane-methanol). The appropriate fractions were collected and evaporated. The residue was crystallized from ethyl acetate and then recrystallized from ethyl acetate to give 50.2 g (76%) of product, mp 139°–140° C.

Analysis:

| | | | |
|---|---|---|---|
| Calculated for $C_{17}H_{21}N_3O$: | 72.05% C | 7.47% H | 14.83% N |
| Found: | 72.02% C | 7.64% H | 14.83% N |

EXAMPLE 25

2-(4-Piperidinyl)-5,6-dihydro-4H-imidazo[4,5,1-ij]quinoline fumarate

A solution of 1-acetyl-4-[5,6-dihydro-4H-imidazo[4,5,1-ij]quinolin-2-yl]piperidine (44.35 g) in 48% hydrobromic acid was stirred under reflux for five hrs. The reaction mixture was chilled to ~5° C., and the precipitate was collected. The solid was suspended in water (200 ml), and the pH 8 was adjusted with sodium bicarbonate solution. The mixture was extracted with chloroform and the combined organic layers were dried over anhydrous magnesium sulfate, filtered, and the filtrate was evaporated. The residue was purified by flash chromatography (silica gel; 2% triethylamine-methanol). The appropriate fractions were collected and evaporated to give 34.5 g (91%) of product free base. The product free base (2.5 g) was dissolved in methanol, treated with a solution of fumaric acid in methanol. The methanol solution was concentrated and crystallization was induced by addition of ether. Recrystallization from methanol-ether gave 2.0 g (76%) of product, mp 224°–225° C.

Analysis:

| | | | |
|---|---|---|---|
| Calculated for $C_{15}H_{19}N_3 \cdot C_4H_4O_4$: | 63.85% C | 6.49% H | 11.76% N |
| Found: | 63.72% C | 6.63% H | 11.64% N |

EXAMPLE 26

5,6-Dihydro-2-(1-piperazinyl)-4H-imidazo[4,5,1-ij]quinoline dihydrochloride

A solution of 4-[5,6-dihydro-4H-imidazo[4,5,1i-ij]quinolin-2-yl]-1-piperazinecarboxaldehyde (18.11 g) in 48% hydrobromic acid (200 ml) was stirred under reflux for 1.5 hrs. The solution was cooled to ambient temperature and basified with 20% sodium hydroxide solution in ice. The aqueous mixture was extracted with dichloromethane, and the combined organic extracts were dried over anhydrous magnesium sulfate, filtered, and the filtrate was evaporated. The residue was purified by flash chromatography (silica gel; 1% triethylamine-methanol). The appropriate fractions were collected and evaporated. The residue was recrystallized from ethanol-ether to give 15.3 g (94%) of product free base, mp 210° C. (dec). Product free base (2.5 g) was taken up in methanol (200 ml) and treated with methanolic hydrogen chloride solution. The resulting solution was concentrated to 100 ml and ether was added to the cloud point. Cooling gave 2.3 g (71%) of product, mp >250° C.

Analysis:

| | | | |
|---|---|---|---|
| Calculated for $C_{14}H_{18}N_4 \cdot 2HCl$: | 53.34% C | 6.40% H | 17.77% N |
| Found: | 53.13% C | 6.62% H | 17.49% N |

We claim:
1. A compound of the formula

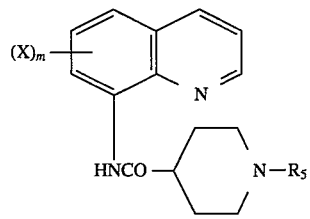

wherein:
(a) X is loweralkyl, loweralkoxy, halogen, or trifluoromethyl and m is 1 or 2 when x is other than hydrogen; and
(b) $R_5$ is a group of the formula $R_6CO$ wherein $R_6$ is hydrogen or loweralkyl.

2. The compound according to claim 1 which is 1-acetyl-N-(quinolin-8-yl)-4-piperidinecarboxamide.

\* \* \* \* \*